United States Patent
Smith (10) Patent No.: US 10,314,473 B2
(45) Date of Patent: Jun. 11, 2019

(54) SYSTEM AND METHOD FOR IN VIVO DETECTION OF FLUORESCENCE FROM AN EYE

(71) Applicant: New York University, New York, NY (US)

(72) Inventor: R. Theodore Smith, New York, NY (US)

(73) Assignee: New York University, New York, NY (US)

( * ) Notice: Subject to any disclaimer, the term of this patent is extended or adjusted under 35 U.S.C. 154(b) by 238 days.

(21) Appl. No.: 15/261,102

(22) Filed: Sep. 9, 2016

(65) Prior Publication Data
US 2017/0065179 A1 Mar. 9, 2017

Related U.S. Application Data

(60) Provisional application No. 62/216,081, filed on Sep. 9, 2015.

(51) Int. Cl.
| | | |
|---|---|---|
| A61B 5/00 | (2006.01) | |
| A61B 3/00 | (2006.01) | |
| A61B 3/12 | (2006.01) | |

(52) U.S. Cl.
CPC ............ *A61B 3/0025* (2013.01); *A61B 3/12* (2013.01)

(58) Field of Classification Search
None
See application file for complete search history.

(56) References Cited

U.S. PATENT DOCUMENTS

| | | | | |
|---|---|---|---|---|
| 4,569,354 A | * | 2/1986 | Shapiro | A61B 3/1241 600/476 |
| 6,733,490 B1 | * | 5/2004 | Falsini | A61F 9/00821 128/898 |
| 7,125,542 B2 | * | 10/2006 | Miller | A61K 38/10 424/9.61 |
| 7,512,436 B2 | * | 3/2009 | Petty | A61B 3/12 351/205 |
| 7,648,239 B2 | * | 1/2010 | Spaide | A61B 3/1233 351/206 |
| 8,303,115 B2 | * | 11/2012 | Ribaric | A61B 3/14 351/200 |

(Continued)

OTHER PUBLICATIONS

Ami et al., "Ex Vivo Hyperspectral Autofluorescence (AF) Imaging of Retinal Pigment Epithelium (RPE) in Human Donor Eyes with Age-related Macular Degeneration (AMD)", Investigative Ophthalmology & Visual Science, vol. 56, Jun. 2015, pp. 4369.

(Continued)

*Primary Examiner* — Brian T Gedeon
(74) *Attorney, Agent, or Firm* — Fay Kaplun & Marcin, LLP (57) ABSTRACT

A system and method for in vivo detection and quantification of drusen present in the retina via administering an excitation signal to the retina of the eye and detecting an electromagnetic emissions spectrum from the retina in response to the excitation signal. The electromagnetic emissions spectrum may be used to identify a plurality of component emissions spectra, each component emissions spectrum corresponding to fluorescence from a component of the retina, one of the component emissions spectra corresponding to a target emissions spectrum.

22 Claims, 6 Drawing Sheets
(3 of 6 Drawing Sheet(s) Filed in Color)

(56) References Cited

U.S. PATENT DOCUMENTS

| | | | |
|---|---|---|---|
| 8,781,559 B2* | 7/2014 | Elner | A61B 3/12 |
| | | | 351/205 |
| 8,896,682 B2* | 11/2014 | Bressler | A61B 3/0025 |
| | | | 348/78 |
| 9,002,085 B1* | 4/2015 | Solanki | G06T 7/0014 |
| | | | 382/128 |
| 9,173,862 B2* | 11/2015 | McKay | A61K 31/00 |
| 9,198,578 B2* | 12/2015 | Zuzak | A61B 5/0071 |
| 9,320,436 B2* | 4/2016 | Russmann | A61B 5/0059 |
| 9,445,715 B2* | 9/2016 | Gierhart | A61B 3/12 |
| 9,798,163 B2* | 10/2017 | Ishak | G02C 7/10 |
| 9,801,955 B2* | 10/2017 | Thompson | G01N 33/58 |
| 9,820,969 B2* | 11/2017 | Boyd | A61K 49/0008 |
| 2003/0004418 A1* | 1/2003 | Marmorstein | A61B 3/12 |
| | | | 600/475 |
| 2006/0099714 A1* | 5/2006 | Mata | A61K 31/355 |
| | | | 436/106 |
| 2008/0221416 A1* | 9/2008 | Baker | A61B 3/10 |
| | | | 600/318 |
| 2016/0067357 A1* | 3/2016 | Francois | C12Q 1/37 |
| | | | 424/9.6 |

OTHER PUBLICATIONS

Tong et al., "Hyperspectral Autofluorescence (AF) Characterization of Drusen in Donor Eyes with Age-Related Macular Degeneration (AMD)", Investigative Ophthalmology & Visual Science, vol. 56, Jun. 2015, pp. 3956.

* cited by examiner

SYSTEM AND METHOD FOR IN VIVO DETECTION OF FLUORESCENCE FROM AN EYE

PRIORITY CLAIM

This application claims priority to U.S. Provisional Application Ser. No. 62/216,081 filed Sep. 9, 2015, the entire contends of which is hereby incorporated by reference herein.

GOVERNMENT FUNDING

This invention was made with government support under Grant Nos. R01 EY021470. The U.S. government has certain rights in the invention.

FIELD OF INVENTION

The present invention relates generally to fluorescent imaging and detection of age-related macular degeneration (AMD) in an eye.

BACKGROUND

Age-related macular degeneration (AMD) has been a major cause in untreatable vision loss and blindness. AMD is a disease of the photoreceptor system in the eye, including undesirable changes to the retinal pigment epithelium (RPE). The RPE is a monolayer of pigmented epithelial cells directly beneath the photoreceptors of the neural retina. It rests on Bruch's membrane (BrM), a 5-layered extracellular matrix, which functions as both the substrate for RPE attachment and as a vessel wall at the inner aspect of the choroidal vasculature that nourishes RPE and photoreceptors. Changes in the RPE are considered to be central to the initiation and progression of AMD, which is a major cause of vision loss in the elderly in the industrialized countries today. The RPE has an innate autofluorescence; the normal pattern of this fluorescence is altered in AMD in characteristic ways. For example, drusen, which are extracellular deposits between the basal lamina of the retinal pigment epithelium (RPE) and the inner collagenous layer of Bruch's membrane (BrM), are believed to be one of the hallmark early signs of AMD. To date, the only treatment for early AMD with drusen is antioxidant supplementation for just a subset of early AMD patients.

Therefore, there is a need for a device that provides for imaging and quantifying the autofluorescence of the eye, particularly for the identification of drusen and its components in the RPE, to identify the biologic and/or molecular basis and to diagnose patients suffering from AMD.

SUMMARY OF THE INVENTION

In accordance with the foregoing objectives and others, one embodiment of the present invention provides systems and methods for in vivo detection of fluorescence from an eye of a patient.

In one aspect, a method for in vivo detection of fluorescence from an eye of a patient is provided. The method includes the step of administering an excitation signal to a retina of the eye, wherein the excitation signal is a short wavelength violet light or a blue light. The method also includes the step of detecting, using one or more hyperspectral sensors, an electro magnetic emissions spectrum from the retina in response to the excitation signal. The method further includes the step of identifying a plurality of component emissions spectra from the electromagnetic emissions spectrum, wherein each component emissions spectrum corresponds to fluorescence from a component of the retina. The method further includes the step of determining whether one of the component emissions spectra corresponds to a target emissions spectrum, wherein the target emissions spectrum extends from a wavelength from about 450 nm to about 580 nm. The method further includes quantifying an amount of drusen present in the retina based on the target emissions spectrum. In one embodiment, the excitation signal has a wavelength from about 400 nm to about 490 nm to a retina of the eye. In another embodiment, the excitation signal has a wavelength of about 436 nm. In another embodiment, the target emissions spectrum has a peak wavelength of about 510 nm. In some embodiments, the quantifying step includes the steps of adjusting the target emissions spectrum based on normative data corresponding to a lens of the eye and analyzing a magnitude or an area under the curve of the adjusted target emissions spectrum to quantify the amount of drusen present in the retina. In a further embodiment, the normative data is selected from a group consisting of (i) population normative data indicative of cataract lens; (ii) population reference data indicative of intraocular lens; and (iii) population normative data indicative of healthy lens. In another embodiment, the method may also include the step of diagnosing the patient with age-related macular degeneration when the amount of drusen quantified is above a predetermined threshold. In another embodiment, the method may further include the step of adjusting a treatment for age-related macular degeneration to the patient based on the amount of drusen quantified.

In another aspect, a hyperspectral imaging device for in vivo detection of fluorescence from an eye of a patient is provided. The device includes a light source configured to deliver in vivo an excitation signal to a retina of the eye, wherein the excitation signal is a short wavelength violet light or a blue light. The device also includes a hyperspectral sensor configured to collect an electromagnetic emissions spectrum from the retina in response to the excitation signal. The device further includes a processing arrangement configured to identify a plurality of component emissions spectra from the electromagnetic emissions spectrum, wherein each component emissions spectrum corresponds to fluorescence from a component of the retina, determine whether one of the component emissions spectra corresponds to a first target emissions spectrum, wherein the first target emissions spectrum extends from a wavelength from about 450 nm to about 580 nm, and quantify an amount of drusen present in the retina based on the first target emissions spectrum. In some embodiments, the processing arrangement is further configured to determine whether one of the component emissions spectra corresponds to a second emissions spectrum, wherein the target emissions spectrum extends from about 480 nm to about 510 nm, and quantifying an amount of macular pigment present in the retina based on the second target emissions spectrum. In one embodiment, the excitation signal has a wavelength from about 400 nm to about 490 nm to a retina of the eye. In another embodiment, the excitation signal has a wavelength of about 436 nm. In a further embodiment, the target emissions spectrum has a peak wavelength of about 510 nm.

In a further aspect, a method for in vivo diagnosis of age-related macular degeneration in an eye of a patient is provided. The method includes the step of administering an excitation signal to a retina of the eye, wherein the excitation signal is a short wavelength violet light or a blue light. The method also includes the step of detecting, using one or more hyperspectral sensors, an electromagnetic emissions spectrum from the retina in response to the excitation signal. The method further includes the step of identifying one or more component emissions spectra from the electromagnetic emissions spectrum, wherein each component emissions spectrum corresponds to fluorescence from a component of the retina. The method further includes the step of determining whether one of the component emissions spectra corresponds to a target emissions spectrum, wherein the target emissions spectrum extends from a wavelength from about 480 nm to about 550 nm. The method further includes the step of diagnosing the patient with age-related macular degeneration when the target peak emission is detected. In some embodiments, the excitation signal has a wavelength from about 400 nm to about 490 nm to a retina of the eye. In one embodiment, the excitation signal has a wavelength of about 436 nm. In another embodiment, the target emissions spectrum has a peak wavelength of about 510 nm.

In a further aspect, a hyperspectral imaging device for in vivo detection of fluorescence from an eye of a patient is provided. The device includes a light source configured to deliver in vivo an excitation signal to a retina of the eye, wherein the excitation signal is a short wavelength violet light or blue light. The device also includes a hyperspectral sensor configured to collect an electromagnetic emissions spectrum from the retina in response to the excitation signal. The device further includes a processing arrangement configured to identify one or more component emissions spectra from the electromagnetic emissions spectrum, wherein each component emissions spectrum corresponds to fluorescence from a component of the retina, determine whether one of the component emissions spectra corresponds to a target emissions spectrum, wherein the target emissions spectrum extends from a wavelength from about 450 nm to about 580 nm, and diagnose the patient with age-related macular degeneration. In some embodiments, the excitation signal has a wavelength from about 400 nm to about 490 nm to a retina of the eye. In one embodiment, the excitation signal has a wavelength of about 436 nm. In another embodiment, the target emissions spectrum has a peak wavelength of about 510 nm.

In a further aspect, a method for quantifying effectiveness of a pharmaceutical treatment for age-related macular degeneration in a patient is provided. The method includes the step of administering a first excitation signal having a wavelength from about 400 nm to about 490 nm to a retina of the eye. The method also includes the step of detecting, using one or more hyperspectral sensors, a first electromagnetic emissions spectrum from the retina in response to the first excitation signal. The method further includes the step of determining a first amount of drusen present in the retina by analyzing the first electromagnetic emissions spectrum to extract a first target emission spectrum from the first electromagnetic emissions spectrum, wherein the first target emission spectrum extends from a wavelength from about 450 nm to about 580 nm, and quantifying the first amount of drusen present in the retina based on the first target emissions spectrum. The method further includes the step of administering a second excitation signal having a wavelength from about 400 nm to about 450 nm to the retina subsequent to administration of the pharmaceutical treatment to the patient. The method further includes the step of detecting, using the one or more hyperspectral sensors, a second electromagnetic emissions spectrum from the retina in response to the second excitation signal. The method further includes the step of determining a second amount of drusen present in the retina by analyzing the second electromagnetic emissions spectrum to extract a second target emission spectrum from the second electromagnetic emissions spectrum, wherein the second target emissions spectrum extends from a wavelength from about 450 nm to about 580 nm, and quantifying the second amount of drusen present in the retina based on the second target emissions spectrum. The method further includes the step of determining the effectiveness of a pharmaceutical treatment for age-related macular degeneration as a function of the first amount and the second amount of drusen detected.

These and other aspects of the invention will become apparent to those skilled in the art after a reading of the following detailed description of the invention, including the figures and appended claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

The RPE is responsible for certain steps in phototransduction, which are biochemical steps that are part of the visual cycle of a patient. Byproducts of the visual cycle, some of which may provide intense fluorescent signals, are thought to aggregate in the lysosomal compartment of the RPE. Because this signal comes from endogenous substances (e.g., fluorophors), rather than, for example, exogenously introduced fluorescent markers, it may be referred to as autofluorescence (AF) of the RPE. The AF of a patient's RPE may be useful in diagnostics and clinical management of retinal disease. The endogenous fluorophores may be excited by an external source of electromagnetic waves in any suitable wavelengths, such as, for example, infrared waves, ultraviolet waves, microwaves, or visible light. In response to such excitation signals, the endogenous fluorophores in the biologic tissue, in particular, the retina or the RPE, may emit electromagnetic waves that are distinctly characteristic of its molecular composition, and thereby providing unique autofluorescence signals that are useful for detection and diagnosis of AMD.

One group of such useful fluorophores may include drusen, which as revealed by ex vivo histochemistry, mass spectrometry, and X-ray microanalysis, have strong components of lipids, including esterified and unesterified cholesterol and phosphatidylcholine, calcium phosphate in the form of hydroxyapatite, and scores of proteins, including apolipoproteins E, B, and J, vitronectin, tissue inhibitor of metalloproteinase-3 (TIMP-3), and many proteins in the complement pathway (e.g., complement factor H and C9). Some components are reflected in genetic associations, especially complement (innate immunity) and TIMP-3 (regulation of extracellular matrix). Drusen can be categorized into "soft" and "hard" types based on their clinical appearance—soft drusen being fatty deposits in the patient's macula that are large and clustered together, and hard drusen being fatty deposits in the patient's macula that are small and far apart. Therefore, hard drusen does not impart a significant impediment to the patient's vision. In contrast, soft drusen can accumulate in the macula and is believe to be an indicator of AMD. However, over the long term (5-20 years), even hard drusen can progress to soft drusen and clinical AMD. The present invention provides an imaging device that provides in vivo detection and/or quantification of drusen in a patient that may be useful in the diagnosis and treatment of AMD, and may also be useful in assessing and/or quantifying effectiveness of potential treatments, e.g., pharmaceutical agents, in the treatment of AMD.

Figure 1A:
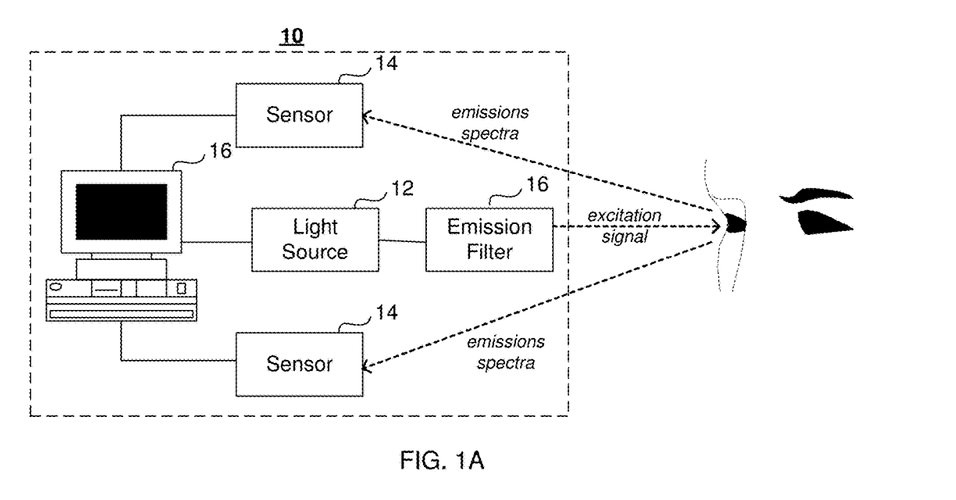
FIG. 1A shows an exemplary hyperspectral imaging device 10 for analyzing fluorescence of fluorophors in the eye.

In one exemplary embodiment, an imaging device 10 for detecting fluorophores, specifically the presence of drusen, in an eye, including the retina, RPE, or sub-RPE regions, may be provided. FIG. 1A shows an exemplary imaging device 10 for detecting and analyzing fluorescence of fluorophores, including drusen, in an eye. The imaging device 10 may be a hyperspectral imaging device and may include one or more sensors 14, e.g., hyperspectral sensors, for collecting hyperspectral data from the fluorophores in the eye. The term "hyperspectral" as used herein generally refers to detection of more than 12 electromagnetic waves closely spaced across a range of wavelengths. Alternatively, the imaging device 10 may be a multi-spectral imaging device having a plurality of sensors 14 for collecting spectra data in a plurality of different wavelengths, generally 3 to 10 in number, from the fluorophores in the eye. For example, the multi-spectral imaging device may be configured to collect spectra data in 4 or more different wavelengths, preferably 6 or more different wavelengths. In one particular embodiment, the multi-spectral imaging device may be configured to collect spectra data in 8 or more different wavelengths.

The device may include a light source 12, e.g., a laser, for delivering at least one excitation signal to the eye. In some embodiments, the device 10 may include one or more light sources 12 for delivering electromagnetic waves having at least two different wavelengths. The light source 12 may be connected to a processing arrangement 16 configured to receive signals instructing the light source 12 for providing an excitation signal to the eye. The excitation signal may comprise light at one or more different suitable wavelengths.

The light source 12 may be coupled to a suitable long pass emission filter 16 that blocks reflected light from the eye, and allows only the fluorescent emission signals from the eye to return. This fluorescent signal may then be captured by one or more of the sensors 14. In particular, sensors 14 may collect hyperspectral data emitted from the eye, in particular, from the fluorophors of the retina, RPE or sub-RPE regions in a patient's eye. The sensors 14 may be connected to the processing arrangement 16. The sensors 14 may be configured to transmit to the processing arrangement 16 hyperspectral and/or multi-spectral emissions data measured from the eye.

As discussed above, the excitation signal may be any suitable electromagnetic waves for excitation of endogenous fluorophores in the eye, specifically the RPE of the eye. For example, the excitation signal may include electromagnetic waves in any suitable wavelengths, such as, for example, infrared waves, ultraviolet waves, microwaves, or visible light. In particular, the excitation signal may include electromagnetic waves having a wavelength in the visible blue and violet light range. Specifically, the excitation signal may include a short wavelength violet light or a blue light. More particularly, the excitation signal may comprise light having a wavelength from about 400 nm to about 490 nm. In particular, the excitation signal may comprise a light having a wavelength of about 436 nm and/or a light having a wavelength of about 480 nm.

In one embodiment of the imaging device 10, the sensors 14 may be hyperspectral sensors that are included in a hyperspectral camera, such as a hyperspectral fundus camera, used to capture electromagnetic emissions from the fluorophors of the eye. In some embodiments, the hyperspectral sensors 14 may be included in a scanning laser ophthalmoscope (SLO), more particularly a confocal scanning laser ophthalmoscope (cSLO), such as the Heidelberg Engineering Spectralis SLO. The SLO or cSLO may also include a snapshot acquisition "per frame" for all recorded emissions wavelengths, and then the average of the snapshots. This average is particularly useful for systems with a low signal to noise ratio where multiple images may be acquired and an average of the images are obtained to identify and eliminate noise from the images. The hyperspectral sensors may also be included in a fundus camera, such as the standard fundus camera adapted for detecting AF from Topcon (e.g., Topcon TRC-501X) or from Zeiss (e.g., Zeiss FF 450 Plus IR). In one particular embodiment, the hyperspectral sensors may be included in a fluorescence microscope, such as a Zeiss Axio Imager A2 microscope. With a single flash, a non-confocal image may be captured as a snapshot hyperspectral image. With non-confocal imaging, an image of the fluorescence may be captured from everything, including the lens, and thus, corrections would need to be made. With confocal imaging, only RPE fluorescence is captured and other sources such as the lens are rejected. The lens AF spectrum may be separated from the RPE signal. Other spectral data, e.g., fundus reflectance, may be used to correct for lens absorbance.

The imaging device 10 may further include any suitable processing arrangement 16 for controlling the light source and/or one or more sensors 14, further analyzing these autofluorescence signals, or identifying and/or quantifying an amount of drusen present in the retina, as described further in the exemplary methods below. Those skilled in the art will understand that the exemplary embodiments described herein may be implemented in any number of manners, including as a separate software module, as a combination of hardware and software, etc. For example, the exemplary analysis methods may be embodied in one or more programs stored in a non-transitory storage medium and containing lines of code that, when compiled, may be executed by at least one of the plurality of processor cores or a separate processor. In some embodiments, a system comprising a plurality of processor cores and a set of instructions executing on the plurality of processor cores may be provided. The set of instructions may be operable to perform the exemplary methods discussed below.

Figure 1B:
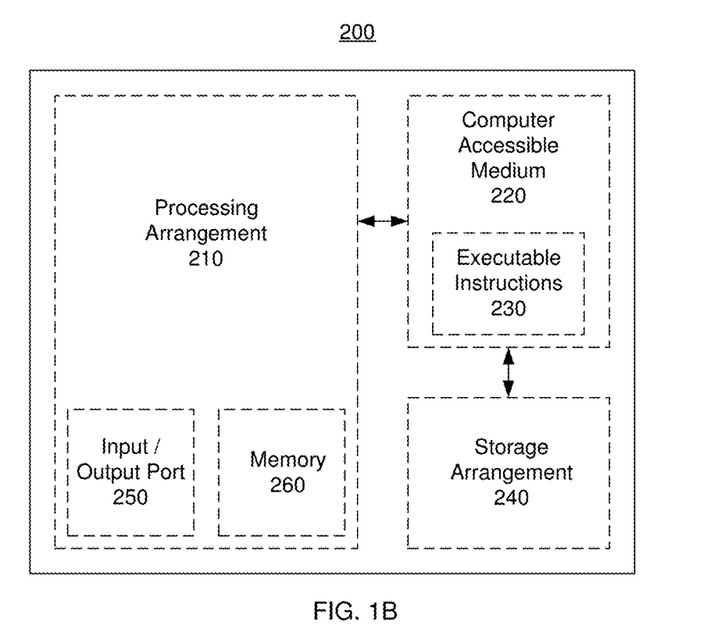
FIG. 1B illustrates an exemplary computer system for performing the method of analyzing fluorescence of retinal components.

For example, the exemplary methods may be embodied in an exemplary system 200 as shown in FIG. 1B. For example, an exemplary method described herein may be performed entirely or in part by a processing arrangement 210. Such processing/computing arrangement 210 may be, e.g., entirely or a part of, or include, but not limited to, a computer/processor that can include, e.g., one or more microprocessors, and use instructions stored on a computer-accessible medium (e.g., RAM, ROM, hard drive, or other storage device). As shown in FIG. 1B, e.g., a computer-accessible medium 220 (e.g., as described herein, a storage device such as a hard disk, floppy disk, memory stick, CD-ROM, RAM, ROM, etc., or a collection thereof) can be provided (e.g., in communication with the processing arrangement 210). The computer-accessible medium 220 may be a non-transitory computer-accessible medium. The computer-accessible medium 220 can contain executable instructions 230 thereon. In addition or alternatively, a storage arrangement 240 can be provided separately from the computer-accessible medium 220, which can provide the instructions to the processing arrangement 210 so as to configure the processing arrangement to execute certain exemplary procedures, processes and methods, as described herein, for example.

System 200 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Figure 2:
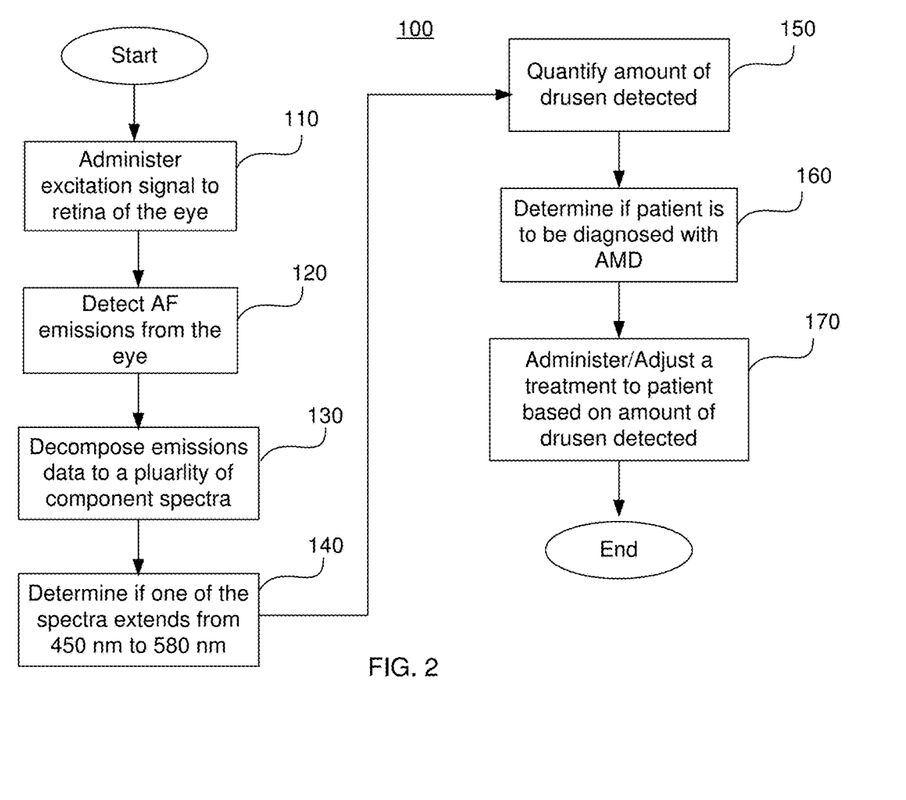
FIG. 2 illustrates an exemplary hyperspectral autofluorescence emission data cube acquired from RPE/BrM tissue oriented in the x,y plane.

FIG. 2 illustrates an exemplary method 100 for detection of fluorescence from an eye of a patient. In particular, the method 100 may be useful for in vivo detection of the presence of drusen, in vivo quantification an amount of drusen present in the retina, the RPE, and/or sub-RPE regions, and/or in vivo diagnosis of AMD in an eye of a patient.

In step 110, at least one excitation signal may be administered in vivo to the eye of the patient. The excitation signal may be any suitable electromagnetic waves for excitation of endogenous fluorophores (e.g., drusen) in the eye, specifically in the retina, RPE or sub-RPE region of the eye. For example, the excitation signal may include electromagnetic waves in any suitable wavelengths, such as, for example, infrared waves, ultraviolet waves, microwaves, or visible light. In particular, the excitation signal may include electromagnetic waves having a wavelength in the visible blue and violet light range. Specifically, the excitation signal may include a short wavelength violet light or a blue light. More particularly, the excitation signal may comprise light having a wavelength from about 400 nm to about 490 nm. Moreover, the excitation signal may comprise a light having a wavelength of about 436 nm and/or a light having a wavelength of about 480 nm.

In step 120, after administration of an excitation signal, an emissions signal may be detected and recorded by one or more hyperspectral or a multi-spectral sensor(s). The emissions signal may be recorded as hyperspectral or multi-spectral emission data across a range of wavelengths. For example, the emissions signal may be recorded in a spectrum having a wavelength from about 420 nm to about 720 nm. In some embodiments, the emissions signals may be recorded and subsequently digitized for further analysis. For example, the emissions signals may be converted to digital data using an analog-to-digital converter (ADC) to generate hyperspectral or multi-spectral emissions data corresponding to the emissions signals detected. The emissions data may be in any suitable format, such as, for example, in the form of a matrix or hypercube.

The excitation of autofluorescence in the eye, in particular, the retina, RPE and/or sub-RPE regions, with multiple wavelengths gives rise to different but closely related spectral data emitted from the same cellular structures. Thus, in step 130, the recorded hyperspectral or multi-spectral emissions data may be decomposed by any suitable component analysis method into a plurality of components, e.g., its major spectral signatures. Each of the plurality of components may represent a component emissions spectrum extending across a predetermined range of wavelengths and having an emissions peak wavelength. Each component emissions spectrum is believed to correspond to autofluorescence of a biologic component in the eye, e.g., lipofuscin, BrM, drusen, etc. Moreover, each of these component emissions spectrum is expected to correspond to identical physiological spatial distributions as they are obtained from the same biologic source, i.e., eye/retina/RPE/sub-RPE region of the patient. In one exemplary embodiment, the emissions data may be decomposed using a principal component analysis (PCA) method, wherein each major spectral signature corresponds to a principal component. In other embodiments, other forms of factor analysis methods, such as, for example, a canonical correlation analysis (CCA) or independent component analysis (ICA), may be used. In another embodiment, a non-negative matrix factorization (NMF) method, constrained non-negative matrix factorization (cNMF) or a non-negative tenser factorization (NTF), such as, for example, those described in U.S. Patent Application Publication No. 2016/0106311, which is incorporated by reference herein, may also be used to decompose the emissions data into a plurality of components. The matrix factorization methods may be supervised or unsupervised. For example, there may be a supervision step that models a subset of the measured spectra, or partially supervises the initial conditions, with Gaussian distributions or known candidate spectra. Each of the components may correspond to a major spectral signature of the eye, including but not limited to Bruch's membrane (BrM), lipofuscin, melanolipofuscin individual components, and drusen.

In step 140, the plurality of components emissions spectra or data corresponding to each of the plurality of components emissions spectra may be further analyzed to determine whether one of the plurality of component emissions spectra is a target emissions spectrum that corresponds to a predetermined emissions profile for a biologic component of the eye. Specifically, the target emissions spectrum may correspond to an emissions profile for drusen in the retina, RPE, and/or sub-RPE region of the eye. More particularly, the target emissions spectrum for drusen in the retina, RPE, and/or sub-RPE region of the eye may extend from about 450 nm to about 580 nm and/or have a peak wavelength of about 510 nm. Specifically, an emissions spectrum peaking at about 510 nm in response to an excitation signal having a wavelength of about 436 nm ($\lambda_{ex}$ 436 nm) appears to be sensitive and specific for drusen and sub-RPE deposits. The sub-RPE deposits are believed to be the same material as drusen, but occur in thin layers beneath the RPE. The sub-RPE depositions are believed to be precursors to drusen and the first histopathological sign of AMD. More specifically, at $\lambda_{ex}$ 436 nm, it has been observed that emissions spectra consistently localized with a peak emission near 510 nm for drusen and sub-RPE deposits. Therefore, detection of a target emissions spectrum within the wavelength range and/or having the same or similar peak emissions wavelength as those consistently observed and localized for drusen may be used to elucidate the presence of drusen within the retina, RPE, and/or sub-RPE region of the patient. If one of the component emissions spectra corresponds to the target emissions spectrum described above, the data corresponding to that the target emissions spectrum may be further analyzed to provide a quantitative measurement corresponding to an amount of the biologic component (e.g., drusen) detected in the patient's eye (step 150). Alternatively, the method 100 may proceed directly to step 160 to determine whether the patient is to be diagnosed with AMD, which is discussed further below.

In step 150, the target emissions spectrum may be analyzed to provide a quantitative measurement corresponding to an amount of biologic component detected in the patient's eye. The amplitude or intensity of the emissions spectrum is believed to be related to the amount of AF biologic material endogenously present in the patient's eye. In one particular embodiment, the target emissions spectrum may correspond to an emissions profile for drusen in the retina, RPE, and/or sub-RPE region of the eye, and may be analyzed to provide a quantitative measurement correspond to an amount of drusen detected in vivo from the retina, RPE, and/or sub-RPE region of the patient's eye. Therefore, the amplitude and/or area under the curve (AUC) for the target emissions spectrum may be analyzed to quantify an amount of biologic component, e.g., drusen, detected in the patient's eye.

In one specific embodiment, to provide a quantitative measurement corresponding to an amount of drusen detected in vivo from a retina, RPE, and/or sub-RPE region of the eye, the target emissions spectrum may be normalized to adjust for different transparencies/opacity of the lens of the patient, which is located in front of the retina and RPE. Excitation signals and AF emissions from the retina RPE, and/or sub-RPE region must traverse the lens of the eye, which can be distorted by various physiological/material properties of the lens, including curvature, spectral optical density, transparency/opacity, composition forming the lens, etc. Therefore, data corresponding to the target emissions spectrum may need to be adjusted and/or normalized such that artifacts and/or variations in the data caused by changes in the lens of the patient are removed, leaving a set of normalized target emissions spectrum data that corresponds to the true level of AF that would be emitted in vivo from the retina RPE, and/or sub-RPE region of the eye in the absence of the lens.

In one particular embodiment, the data corresponding to the target emissions spectrum may be adjusted based on normative data corresponding to a type of lens in the patient's eye, which may be stored in one or more databases. For example, patient's target emissions spectrum may be adjusted based on normative data indicative of various different conditions of a lens in the patient's eye. The normative data may be indicative of AF for a population of patients having the select type of lens in the eye. For example, the database may include one or more sets of normative data each corresponding to a different type of lens in the patient's eye, such as, for example: (1) healthy human lenses in patients under the age of 60; (2) healthy human lenses in patients over the age of 60; (3) healthy human lenses regardless of age; (4) human lenses from patients having cataracts who have not undergone any form of surgery; (5) human lenses from patients who have undergone cataract surgery without an artificial lens replacement; and (6) human lenses from patients who have undergone an artificial lens replacement. For patients who have undergone an artificial lens replacement, the normative data may be specific for each type of artificial lens suitable for implantation in the eye. In particular, the spectral optical density of each type of artificial lens may be obtained ex vivo (e.g., prior to implantation or from the manufacturer of the artificial lens) and used to adjust in vivo target emissions spectrum data. Those skilled in the art will understand that the term database is not being used to connote a specific data structure. Rather, it is to be understood broadly to include any searchable collection of data records residing in any type of memory.

The normalized target emissions spectrum data may be further analyzed to determine a quantitative measurement corresponding to an amount of biologic component, e.g., drusen, detected in vivo from the retina, RPE or sub-RPE region of the patient's eye. The normalized target emissions spectrum data may be quantified in any suitable manner, for example, a quantitative value may be determined based on the amplitude of the peak of the target emissions spectrum. In another example, the normalized target emissions spectrum data may be quantified by determining an AUC for the target emissions spectrum. To determine the amount of drusen detected in vivo from the eye of the patient, this quantitative value may first be calibrated to simultaneously measured emission from a fluorescent standard material that has been excited by the same light that was used in the eye of the patient. This further quantified value is known as the quantitative hyperspectral autofluorescence (qHAF) measurement of the target emissions spectrum. Similar qHAF measurements may also be made of the other emissions spectra. The qHAF measure of the target emissions spectrum may then be compared to a standardized scale, wherein the quantitative value for an emissions spectrum corresponds to a standardized and known amount of drusen. The standardized scale may be generated by obtaining emissions spectra data for a plurality of samples, each having a known amount of drusen. The quantitative value, e.g., amplitude of the peak or AUC, may be correlated to the amount of drusen in each of the standard samples and thereby, forming a standardized scale that correlates the quantitative values of emissions spectra to amounts of drusen detected. The quantitative measurement corresponding to an amount of biologic component, e.g., drusen, obtained based on the normalized target emissions spectrum data may be used to provide a diagnosis (step 160) or to administer/titrate a treatment for AMD (step 170).

The amount of drusen accumulated in the patient's retina RPE, and/or sub-RPE region is believed to correspond to increased risk of AMD, onset of AMD, or different states of AMD disease progression in the eye. For example, in a healthy eye, drusen is expected to be absent. In an eye of a patient diagnosed with AMD, portions of the retina, RPE, and/or sub-RPE region may include drusen deposits, and thus, quantifying the amount of drusen accumulated in the retina, RPE, and/or sub-RPE region may provide a quantitative measurement that corresponds to progression of AMD in the eye of the patient, e.g., the extent of drusen accumulations in the eye or extent of vision loss of the eye, which may reflect AMD disease progression. The method 100 for detection of an AF emissions spectra corresponding to drusen in the retina, RPE, and/or sub-RPE region of the eye provides an in vivo method that can be useful for early diagnosis of risks and/or development of AMD, monitoring the progression of a patient with AMD, and/or monitoring treatment of a patient with AMD. In particular, the AF emissions spectra corresponding to an amount of drusen in the eye that may be detected and analyzed to quantify the amount of drusen accumulated in the retina, RPE, and/or sub-RPE region in the eye and help diagnose and/or identify progression of AMD in a patient. Furthermore, the in vivo method 100 described herein may be configured to detect low amounts of drusen accumulated within the retina that was not detectable using previous techniques. For example, in the exemplary methods described herein, drusen and their precursor sub-RPE deposits are detected by their molecular AF signal. This does not require the drusen to be physically large enough to be seen on techniques like fundus photography or optical coherence tomography (OCT). In particular, the thin sheets of sub-RPE deposits cannot be visualized by these other methods.

In step 160, a diagnosis of the patient's progression of AMD may be determined based detection of the target emissions spectrum (step 140), a quantitative value correlated to an amount of drusen detected (step 150), and/or an amount of drusen detected (step 150). In one embodiment, if the target emissions spectrum is detected in the patient's emissions data, the patient may be diagnosed with an increased likelihood for AMD or as already suffering from AMD. In another embodiment, a predetermined threshold value for either the quantitative value correlated to the amount of drusen detected or the amount of drusen detected may be used. Specifically, if the patient's in vivo emissions data, after analysis in steps 140 and 150, is determined to have a quantitative value or amount of drusen detected above the predetermined threshold value, the patient may be diagnosed as having an increased risk for AMD or as already suffering from AMD. The predetermined threshold values may be at or about 0.025 mm$^3$ of drusen, and therefore, if the in vivo emissions data indicates that more than about 0.025 mm$^3$ of drusen is present in the patient's retina, RPE and/or sub-RPE region, the patient may be at an increased risk for AMD, or as already suffering from AMD. In an alternative embodiment, a plurality of predetermined threshold values may be used to assess the patient's progression of AMD. For example, if the in vivo emissions data indicates that less than about 0.025 mm$^3$ of drusen is detected in the patient's retina, RPE, and/or sub-RPE region, the patient may not be be suffering from or be at an increased risk of developing AMD in the near future. If the in vivo emissions data indicates that more than about 0.025 mm$^3$ of drusen is detected in the patient's retina, RPE and/or sub-RPE region, the patient may be at risk of developing AMD in the near future. If the in vivo emissions data indicates that more than about 0.025 mm$^3$ of drusen is detected in the patient's retina, RPE and/or sub-RPE region, the patient may already be within an early stage of AMD. If the in vivo emissions data indicates that more than about 0.025 mm$^3$ of drusen detected in the patient's retina, RPE and/or sub-RPE region, the patient may have progressed to a later stage of AMD, such as intermediate AMD. Emissions data may be correlated to an established metric, the cube root of drusen volume (CRDV) on spectral domain-OCT, reported to have measurements from 0.23 to 0.72 mm (smallest to largest quintiles). Research has shown that risk of progression of AMD is correlated to CRDV at baseline, by quintile [Gregori G, Wang F, Rosenfeld P J, Yehoshua Z, Gregori N Z, Lujan B J, Puliafito C A, Feuer W J. "Spectral domain optical coherence tomography imaging of drusen in nonexudative age-related macular degeneration." Ophthalmology. 2011 July; 118(7):1373-9). The exemplary methods as described herein is believed to be be able to assess drusen more sensitively and show that a patient's quintile score needed to be adjusted upwards, hence confirming higher risk.

In step 170, a treatment for AMD may be initiated, administered and/or adjusted a treatment for AMD based the quantitative measurement corresponding to an amount of biologic component, e.g., drusen, obtained based on the normalized target emissions spectrum data (step 150). In one embodiment, the method 100 may proceed directly to step 170 from obtaining the quantitative measurement in step 150. In an alternative embodiment, the method 100 may first provide a diagnosis (step 160) and subsequently proceed to step 170 to initiate, administer and/or adjust a treatment for AMD based on the quantitative measurement from step 150. The treatment for AMD may include any suitable procedure and/or administration of any suitable pharmaceutical active agent for slowing the progression of, ameliorating, treating, preventing and/or inhibiting AMD. Suitable procedures may include, for example, laser treatments or intravitreal injections. In addition, suitable pharmaceutical active agents may include, for example, lipid lowering agents, in particular agents directed against HDL, LDL, or VLDL, or triglycerides, in any combination. In some embodiments, the quantitative measurement of drusen from step 150 may serve as a trigger for initiating treatment when the measurement is above a predetermined threshold value. In other embodiments, the quantitative measurement of drusen from step 150 may be serve as a trigger for increasing a treatment, e.g., increasing an amount of a pharmaceutical agent administered when the measurement is above a first predetermined threshold value, and/or for decreasing the treatment when the measurement is below a second predetermined threshold value. In a further embodiment, the quantitative measurement of drusen from step 150 may be used to titrate an amount of pharmaceutical active agent to be administered to the patient. The quantitative measurements of drusen may be obtained periodically from the patient to measure progression of AMD more accurately, to measure effectiveness of treatment and/or to personalize and titrate treatment to a particular patient over a period of time, e.g., a week, a month, 3 months, a year, etc. These measurements may be used as endpoints in clinical trials for AMD to determine efficacy (see below).

In some embodiments, the plurality of components of the hyperspectral or multi-spectral emissions data as obtained in step 130 may also include a second target emission spectrum that corresponds to a predetermined emissions profile for macular pigmentation in the retina, RPE and/or sub-RPE region of the eye. The second target emissions spectrum may be further analyzed in a manner similar to step 150 above to quantified the amount of macular pigmentation in the eye. Therefore, the quantitative measurement corresponding to an amount of macular pigmentation detected in the patient's eye may also be used in steps substantially similar to steps 160 and 170 as described above for determining if the patient is to be diagnosed a patient's progression of an ophthalmological disease or condition and/or initiate, administer and/or adjust a treatment for an ophthalmological disease or condition based on the quantitative measurement corresponding to an amount of macular pigmentation obtained from step 150.

The present invention may also be useful in assessing and quantifying effectiveness of a treatment for AMD, including any suitable procedure and/or administration of any suitable pharmaceutical active agent for slowing the progression of, ameliorating, treating, preventing and/or inhibiting AMD. For example, the present invention may be used to monitor patient response to treatment for AMD in clinical trials and thereby providing a quick and quantitative assessment of effectiveness of potential treatment candidates. In one exemplary embodiment, the present invention may be used to assess a quantitative measurement corresponding to an amount of drusen prior to administration of a treatment, during a course of treatment, and/or after administration of treatment. For example, a comparison of a first amount of drusen in the retina, RPE, and/or sub-RPE region of the patient's eye pre-administration of a pharmaceutical treatment with a second amount of drusen in the retina, RPE, and/or sub-RPE region of the patient's eye post-administration of pharmaceutical treatment may determine effectiveness of the treatment for AMD.

Figure 6:
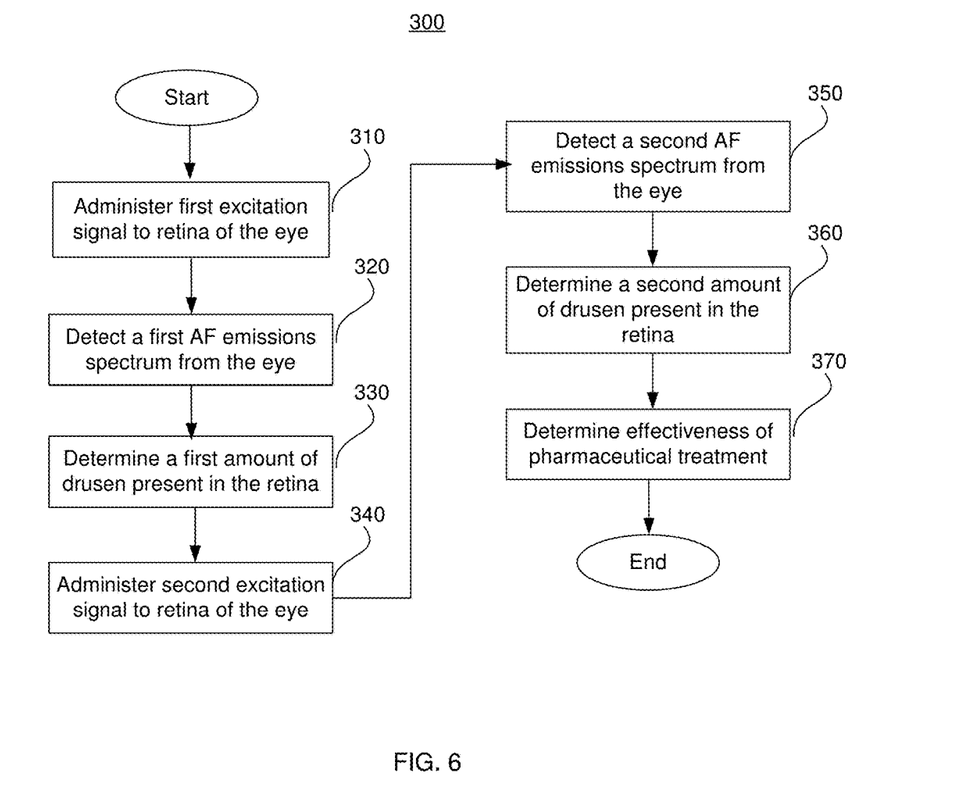
FIG. 6 illustrates an exemplary method for quantifying effectiveness of a treatment for AMD in a patient.

FIG. 6 illustrates an exemplary method 300 for quantifying effectiveness of a treatment for AMD in a patient. In particular, the method 300 may be useful for in vivo quantification of effectiveness of treatment based on the amount of drusen present in the retina, RPE, and/or sub-RPE region in the patient's eye. The treatment for AMD may include any suitable procedure and/or administration of any suitable pharmaceutical active agent for slowing the progression of, ameliorating, treating, preventing and/or inhibiting AMD, as set forth above.

In step 310, a first excitation signal is administered in vivo to the eye of the patient as described in step 110 above. The excitation signal may be any suitable electromagnetic wave for excitation of endogenous flourophores in the eye, specifically in the retina, RPE, and/or sub-RPE region of the eye. More particularly, the excitation signal may include a violet light or a blue light having a wavelength from about 400 nm to about 490 nm.

In step 320, after administration of the first excitation signal, a first emissions signal may be detected and recorded by one or more hyperspectral or a multi-spectral sensor, in accordance with step 120 described above. For example, emissions signal may be recorded as hyperspectral or multi-spectral emission data across a range of wavelengths.

In step 330, the first electromagnetic emissions spectrum is decomposed and analyzed to determine a first amount of drusen present in the retina, RPE, and/or sub-RPE region of the patient's eye. In accordance with step 130 above, the emissions data may be decomposed by any suitable component analysis method into a plurality of components emission spectra. Then, as described in step 140 above, the plurality of components emission spectra may be further analyzed to determine if one of the component emission spectra corresponds to the target emissions spectrum for drusen, such as an emissions spectrum extending from 450 nm to about 580 nm and/or has a peak wavelength of about 510 nm. The target emissions spectrum may then be further analyzed to quantify a first amount of drusen detected in the patient's eye as described in step 150 above.

In step 340, a second excitation signal is administered in vivo to the eye of the patient as described above, in a similar manner as described in step 120 above, after administration of a treatment to the patient. The treatment may include any suitable procedure and/or administration of any suitable pharmaceutical active agent for slowing the progression of, ameliorating, treating, preventing and/or inhibiting AMD. For example, treatment may include drug therapy, laser therapy, or any other known treatment. In an exemplary embodiment, the excitation signal may include a violet light or a blue light having a wavelength from about 400 nm to about 490 nm.

In step 350, after administration of the second excitation signal, a second emissions signal may be detected and recorded by one or more hyperspectral or a multi-spectral sensor in response to the second excitation signal, similar to step 120 described above.

In step 360, similar to step 330, the second electromagnetic emissions spectrum is decomposed and analyzed to determine a second amount of drusen present in the retina, RPE, and/or sub-RPE region of the patient's eye. The emissions data may be decomposed by any suitable component analysis method into a plurality of components emission spectra. The plurality of components emission spectra may be further analyzed to determine if one of the component emission spectra corresponds to the target emissions spectrum for drusen extending from 450 nm to about 580 nm and/or has a peak wavelength of about 510 nm. The target emissions spectrum may then be further analyzed to quantify a second amount of drusen detected in the patient's eye post-administration of the treatment.

In step 370, once the drusen present in the retina, RPE, and/or sub-RPE region of the patient's eye after administration of a treatment is quantified, effectiveness of the treatment for AMD is determined as a function of the first amount of drusen and the second amount of drusen. For example, if the amount of drusen present post-treatment is less than the amount present prior to treatment, it may be realized that the treatment being used is effective in reversing the effects of AMD. In another example, if the first and second amounts of drusen measured are approximately the same, the treatment may be effective in preventing the progression of AMD in the eye. A larger amount of drusen post-treatment would indicate that the treatment may not be effective as applied.

In an alternative embodiment, a method for quantifying effectiveness of a treatment may also provide in vivo quantification of effectiveness of treatment based on the amount of macular pigmentation present in the patient's eye in a substantially similar manner as described above in method 300 with respect to drusen.

EXAMPLES

Example I: Drusen Spectra from 2 Excitation Datasets

Step 1—Administration of Excitation Signal and Detection of Electromagnetic Emissions Spectrum The autofluorescence spectrum of flatmounts of human RPE attached to Bruch's membrane (RPE/BrM) without any retinal pathology was acquired and measured. From chorioretinal tissue, retina and choroid were gently removed to prepare RPE/BrM flat mounts from 5 AMD donor tissues. AMD stage was defined at the time of accession using stereo color photographs and the criteria of the Alabama Age-Related Maculopathy Grading System and confirmed by expert evaluation of the entire flat-mounted macula. Some tissues were also examined using ex vivo spectral-domain optical coherence tomography (acquired with the Spectralis OCT, Heidelberg Engineering, Heidleberg, Germany) to confirm the presence of drusen and abnormal hypo/hyperAF.

Twelve locations with drusen from the 5 AMD donors were imaged using wide-field epi-fluorescence microcopy. A total of 25 drusen were analyzed: 12 small (≤63 um diameter), 8 intermediate (64-124 um), and 5 large (≥125 um).

Microscopy was performed using Zeiss Axio Imager A2 microscope, equipped with a 40× oil lens (NA=1.4) (both: Carl Zeiss, Jena, Germany), two filter cubes (filter 1: 436/460 nm excitation/long pass emission; filter 2: 480/510 nm excitation/long pass emission; Chroma Technology Corp, Bellows Falls, Vt., US) and connected to an external mercury arc light source (X-cite 120Q, Lumen Dynamics Group Inc., Mississauga, Canada).

At each of two excitation wavelengths, one hyperspectral data cube of RPE/BrM was acquired using the two different microscope filters and a hyperspectral camera (Nuance FX, Caliper Life Sciences, Waltham, Mass., US), with measurements made at 10 nm intervals between 420 nm and 720 nm. The data in the smaller spectral range was padded with zeroes to create hypercubes with the same spatial and spectral dimensions. Each raw data cube was saved using the integrated software (Nuance 3.0.1.2.) and exported for further NMF analysis. For brevity, the two excitation wavelengths are referred to herein as 436 nm and 480 nm.

Step 2—Image Registration

All hypercubes were inspected for precise registration of the 2-dimensional spatial slices. In some instances, there was a small linear drift within a hypercube and/or a single linear shift between the hypercubes associated with the 2 excitation wavelengths. These shifts were presumably due to displacements in microscope optics during image acquisition. Subtle nonlinear "barrel"-type distortions were also observed between slices at different emission wavelengths, presumably due to chromatic aberrations. These shifts were corrected with rigid body and nonlinear registration algorithms.

Step 3—Non-Negative Tensor Factorization Image Analysis

RPE/BrM flat mounts were excited at more than one wavelength. As described above, the RPE/BrM flat mounts were excited at both 436 nm and 480 nm, and hyperspectral emission data were captured for both wavelengths. Spectral signatures for RPE/BrM were retrieved for each dataset. Each signal found at 436 nm excitation was paired to a signal at 480 nm and it is assumed that the spatial source distributions of these signals are the same because they come from the same compound.

Figure 3:
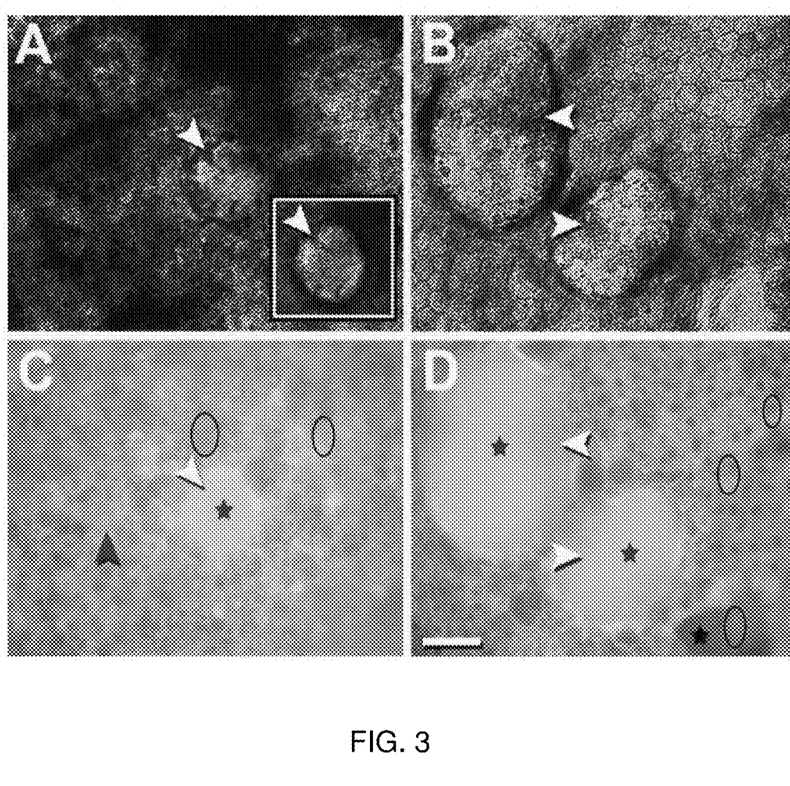
FIG. 3 illustrates an exemplary bright field and corresponding composite hyperspectral autofluorescence images of drusen in RPE/BrM flat mounts from donors with AMD viewed at excitation wavelength 436 nm.
Figure 4A:
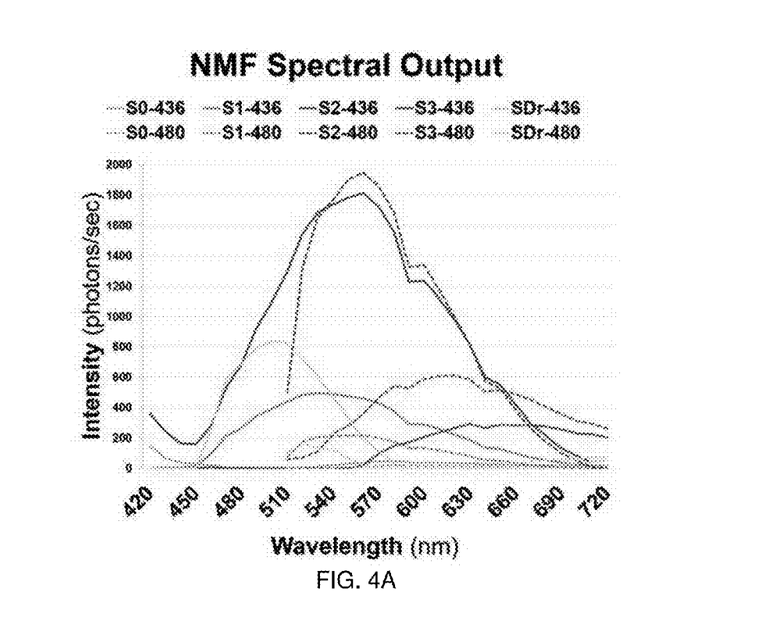
FIG. 4A illustrates an exemplary embodiment of components generated using a single non-negative tensor factorization (NTF) spectra recovery method from tissue with small and intermediate drusen.
Figure 4B:
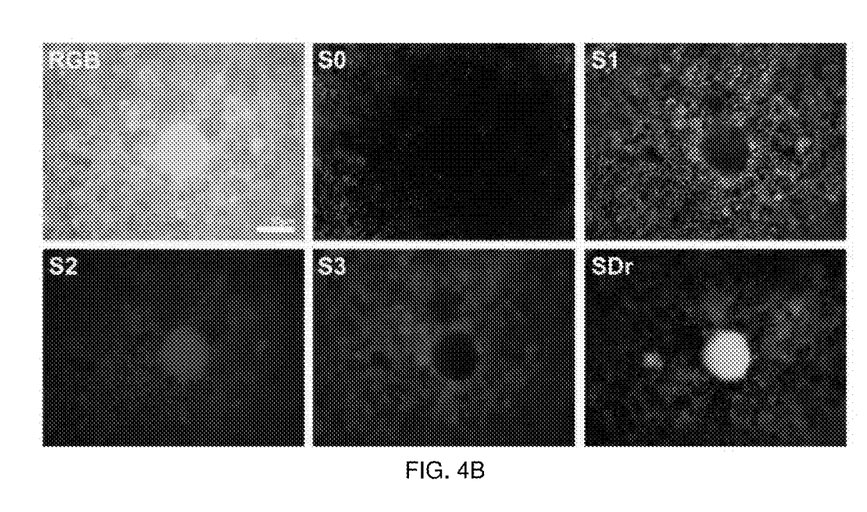
FIG. 4B illustrates an exemplary embodiment of two-dimensional abundance images of components of data of FIG. 4A from an exemplary RPE spectrum received from 436 nm excitation.
Figure 5A:
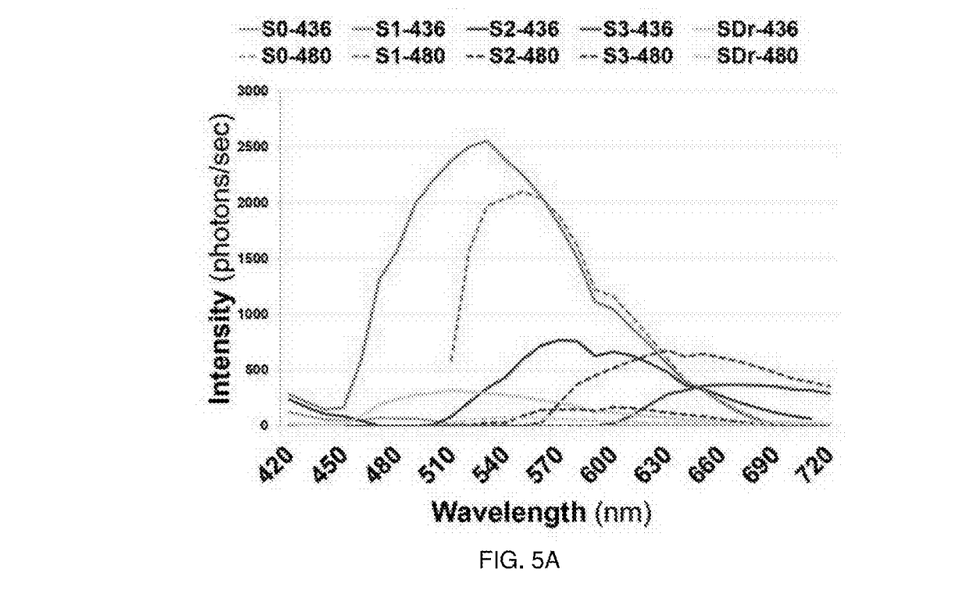
FIG. 5A illustrates another exemplary embodiment of components generated using a single non-negative tensor factorization (NTF) spectra recovery method from tissue with large drusen.
Figure 5B:
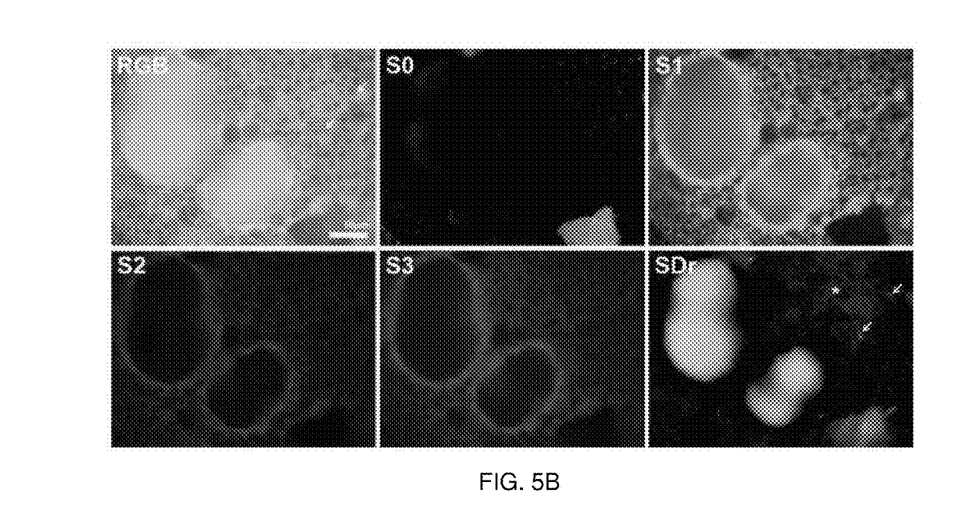
FIG. 5B illustrates an exemplary embodiment of two-dimensional abundance images of components of data of FIG. 5A from an exemplary RPE spectrum received from 436 nm excitation.

FIGS. 4A, 4B, 5A and 5B show data for two different tissues for the corresponding spectra found with simultaneous solutions of the datasets. The NTF solutions for each tissue was initialized with 4 Gaussian-shaped spectra from RPE and one from BrM for each excitation hypercube to search for 5 abundant spectra from each hypercube, in accordance with step 130 above. In other words, data for the spectra in FIGS. 4A-5B are decomposed from simultaneous solution of both excitation datasets, e.g., data obtained from excitation at both 436 nm and 480 nm. FIGS. 4A, 4B show data for spectrum recovered from 436 and 480 nm excitations in small and intermediate drusen. FIGS. 5A, 5B show data for spectrum recovered from 436 and 480 nm excitations in large drusen. The tissue image for the FIGS. is a full 40× field. The 10 individual spectra in FIGS. 4A and 5A are labeled S0-S3 and SDr. The corresponding abundance images of FIGS. 4B and 5B are also labeled S0-S3 and Sdr with false coloring to indicate the relative signal intensities. The spectra shown in the figures are all broad, as can be expected from known fluorophore data, and can be paired by shape and location. The top left element of FIGS. 4B and 5B is the composite RGB image from the total AF signal for the excitation, also seen in FIG. 3.

In FIG. 4B, S2 is abundant in the central druse but is not detectable in the tiny druse (dark arrowhead, FIG. 3, image C). S1 and S3, however, are nearly absent from both, and their spectral strengths (FIG. 4A) in the tissue overall are likewise much less than that of S2. S1 and S3, however, form strong haloes in the RPE around the larger druse and are also present in granules overlying it. SDr strongly localizes to drusen. S0 (BrM) shines through some RPE nuclei but does not localize to the drusen.

In FIG. 5B, S1 is moderately abundant in the drusen, whereas S2 and S3 are nearly absent. Their total spectral lengths (FIG. 5A) are likewise much less than that of S1. S2 and S3, however, form strong haloes in the RPE around the drusen, perhaps in RPE cells draped over the drusen margins. S2 and S3 are also present in granules overlying the drusen. With regard to sub-RPE deposits and BrM, which are both present in the patch in the lower right of the micrographs, S0 and SDr are both present. S0 localizes homogeneously exactly to the area of the patch, while SDr is inhomogeneous, appearing brighter in areas of brighter green on the RGB image, consistent with sub-RPE deposits. S0 also shines through several nuclei but does not localize to the drusen. SDr strongly localizes to the drusen and other flecks of sub-RPE deposit, as indicated by the white arrows) that are indentified on the composite RGB image. Irregula patches of additional SDr (white asterisk) may correspond to sub-RPE deposits partly screened by the RPE itself. However, abundances of RPE spectra S1, S2 and S3 are completely dark (spectra not present) in the area of BrM and sub-RPE deposit.

Step 4—Emission Spectra Identification

In accordance with step 140 described above, 5 different spectra from the electromagnetic emissions spectrum are recovered at the two different wavelengths, as can be seen in FIGS. 4A and 5A. Identification of these different spectra is possible by comparison of these spectrum to known spectral characteristics of RPE and BrM. As noted before, in normal tissue three spectra attributable to RPE L/ML as S1, S2 and S3 have been identified, as well as one spectra attributable to BrM as S0. Here, in 9/12 AMD tissues with drusen, S1 at 436 nm peaked similarly and strongly at 530±10 nm, as can be seen in FIGS. 4A and 5A. The second abundant constituent of normal RPE, S2, was also represented in AMD tissues, peaking at 570 nm with either excitation, a slightly shorter wavelength than in normal tissues (575 nm). The third abundant spectral constituent of normal RPE, S3, was also present in AMD tissues. Like S3 in normal retinas, S3 in AMD eyes had a broad tri-modal spectrum either with a central flat peak around 620 nm and secondary shoulders at 575 and 650 nm or, as is more common for S3 in normal tissues excited at 436 nm, with the actual peak around 650 nm and secondary shoulders at 575 and 620 nm. It is noted that S3 in normal eyes is non-zero across the visible spectrum. Finally, in normal tissues, the BrM spectrum peaked at 490 nm, being non-zero throughout the full 420-720 nm range. Although BrM spectral abundances in AMD tissues were found to be markedly lower in intensity relative to normal tissue, the BrM spectrum was similarly flat without a well-defined peak.

Example 2—Drusen Spectra Identified

Example II focuses on the identification of the drusen spectrum in RPE/BrM tissue excited at 2 different wavelengths: 436 and 480 nm. As provided above, twelve locations with drusen from 5 AMD donors were imaged and analyzed. The two sets of hyperspectral data obtained at each excitation were analyzed using the NTF algorithm to decompose the emission data to 5 component spectra and component localizations in each tissue. Two-dimensional abundance images of the emissions spectrum was obtained at each wavelength. Composite images shown in FIG. 3 annotate tissue components while FIGS. 4A, 5A shows the spectra recovered in the of the donor tissues and FIGS. 4B, 5B show the recovered abundances and spatial origin (localization) of the corresponding spectrum of that same tissue in histologic detail. It is noted that FIGS. 4A, 4B correspond to images A, C from FIG. 3 while FIGS. 5A, 5B correspond to images B, D from FIG. 3.

Analysis of the spectra recovered from the exemplary donor tissue and the corresponding abundance images clearly showed an emission spectrum corresponding specifically to drusen. The emission spectra (SDr) of drusen and sub-RPE deposits from 2 donor tissues at each excitation are denoted by azure curves in spectral output panels of FIG. The corresponding azure abundance images show localization of these signals strictly to the drusen and sub-RPE deposits, with no localization to RPE or BrM (herein, BlamD and BlinD are collectively called sub-RPE deposits, as definitive separation requires transmission electron microscopy or high-resolution light microscopy). Thus, the SDr was identifiable as specific to drusen and sub-RPE deposits.

Looking at the data from all 12 locations, the observed spectral peak of SDr at 436 nm was 510 nm in 10/12 tissues, with other 2 peaks at 500 nm and 490 nm. There were also consistently weaker emissions from drusen excited at 480 nm with most peaks appearing at 520 nm. These were similarly shaped signatures that appeared to be 100% specific for drusen and sub-RPE deposits in all 12 tissues. Because all drusen and sub-RPE deposits within the 25 drusen analyzed exhibited the same signal, which were strictly localized to the drusen and sub-RPE deposits, the discovered spectra appear to be sensitive and specific to drusen, providing novel data for drusen identification in AMD-affected eyes.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art form the foregoing description. Such modifications are also intended to fall within the scope of the appended claims. All publications cited herein are incorporated by reference in their entirety.

What is claimed is:

1. A method for in vivo detection of fluorescence from an eye of a patient, comprising:
  administering an excitation signal to a retina of the eye, wherein the excitation signal is a short wavelength violet light or a blue light;
  detecting, using one or more hyperspectral sensors, an electromagnetic emissions spectrum from the retina in response to the excitation signal;
  identifying a plurality of component emissions spectra from the electromagnetic emissions spectrum, wherein each component emissions spectrum corresponds to fluorescence from a component of the retina separate from spectral characteristics of a retinal pigment epithelium (RPE) and a Bruch's membrane (BrM) of the patient's eye;
  determining whether one of the component emissions spectra corresponds to a target emissions spectrum, wherein the target emissions spectrum extends from a wavelength from about 450 nm to about 580 inn; and
  quantifying an amount of drusen present in the retina based on the target emissions spectrum.

2. The method of claim 1, wherein the excitation signal has a wavelength from about 400 nm to about 490 nm to a retina of the eye.

3. The method of claim 1, wherein the excitation signal has a wavelength of about 436 mm.

4. The method of claim 1, wherein the target emissions spectrum has a peak wavelength of about 510 nm.

5. The method of claim 1, wherein the quantifying step includes:
  adjusting the target emissions spectrum based on normative data corresponding to a lens of the eye; and
  analyzing a magnitude or an area under the curve of the adjusted target emissions spectrum to quantify the amount of drusen present in the retina.

6. The method of claim 5, wherein the normative data is selected from a group consisting of (i) population normative data indicative of a cataract lens; (ii) population reference data indicative of an intraocular lens; and (iii) population normative data indicative of a healthy lens.

7. The method of claim 1, further comprising:
  diagnosing the patient with age-related macular degeneration when the amount of drusen quantified is above a predetermined threshold.

8. The method of claim 1, further comprising:
  adjusting a treatment for age-related macular degeneration to the patient based on the amount of drusen quantified.

9. A hyperspectral imaging device for in vivo detection of fluorescence from an eye of a patient, comprising:
  a light source configured to deliver in vivo an excitation signal to a retina of the eye, wherein the excitation signal is a short wavelength violet light or a blue light;
  a hyperspectral sensor configured to collect an electromagnetic emissions spectrum from the retina in response to the excitation signal; and
  a processing arrangement configured to identify a plurality of component emissions spectra from the electromagnetic emissions spectrum, wherein each component emissions spectrum corresponds to fluorescence from a component of the retina separate from spectral characteristics of a retinal pigment epithelium (RPE) and a Bruch's membrane (BrM) of the patient's eye, determine whether one of the component emissions spectra corresponds to a first target emissions spectrum, wherein the first target emissions spectrum extends from a wavelength from about 450 nm to about 580 nm, and quantify an amount of drusen present in the retina based on the first target emissions spectrum.

10. The hyperspectral imaging device of claim 8, wherein the processing arrangement is further configured to determine whether one of the component emissions spectra corresponds to a second emissions spectrum, wherein the target emissions spectrum extends from a wavelength from about 480 nm to about 510 nm, and quantifying an amount of macular pigment present in the retina based on the second target emissions spectrum.

11. The hyperspectral imaging device of claim 8, wherein the excitation signal has a wavelength from about 400 nm to about 490 nm to a retina of the eye.

12. The hyperspectral imaging device of claim 8, wherein the excitation signal has a wavelength of about 436 nm.

13. The hyperspectral imaging device of claim 8, wherein the target emissions spectrum has a peak wavelength of about 510 nm.

14. A method for in vivo diagnosis of age-related macular degeneration in an eye of a patient, comprising:
- administering an excitation signal to a retina of the eye, wherein the excitation signal is a short wavelength violet light or a blue light;
- detecting, using one or more hyperspectral sensors, an electromagnetic emissions spectrum from the retina in response to the excitation signal;
- identifying one or more component emissions spectra from the electromagnetic emissions spectrum, wherein each component emissions spectrum corresponds to fluorescence from a component of the retina separate from spectral characteristics of a retinal pigment epithelium (RPE) and a Bruch's membrane (BrM) of the patient's eye;
- determining whether one of the component emissions spectra corresponds to a target emissions spectrum, wherein the target emissions spectrum extends from a wavelength from about 450 nm to about 580 nm; and
- diagnosing the patient with age-related macular degeneration when the target peak emission is detected.

15. The method of claim 14, wherein the excitation signal has a wavelength from about 400 nm to about 490 nm to a retina of the eye.

16. The method of claim 14, wherein the excitation signal has a wavelength of about 436 nm.

17. The method of claim 14, wherein the target emissions spectrum has a peak wavelength of about 510 nm.

18. A hyperspectral imaging device for in vivo detection of fluorescence from an eye of a patient, comprising:
- a light source configured to deliver in vivo an excitation signal to a retina of the eye, wherein the excitation signal is a short wavelength violet light or a blue light;
- a hyperspectral sensor configured to collect an electromagnetic emissions spectrum from the retina in response to the excitation signal; and
- a processing arrangement configured to identify one or more component emissions spectra from the electromagnetic emissions spectrum, wherein each component emissions spectrum corresponds to fluorescence from a component of the retina separate from spectral characteristics of a retinal pigment epithelium (RPE) and a Bruch's membrane (BrM) of the patient's eye, determine whether one of the component emissions spectra corresponds to a target emissions spectrum, wherein the target emissions spectrum extends from a wavelength from about 450 nm to about 580 nm, diagnose the patient with age-related macular degeneration when the target peak emission is detected.

19. The hyperspectral imaging device of claim 18, wherein the excitation signal has a wavelength from about 400 nm to about 490 nm to a retina of the eye.

20. The hyperspectral imaging device of claim 18, wherein the excitation signal has a wavelength of about 436 nm.

21. The hyperspectral imaging device of claim 18, wherein the target emissions spectrum has a peak wavelength of about 510 nm.

22. A method for quantifying effectiveness of a pharmaceutical treatment for aged-related macular degeneration in a patient comprising:
- administering a first excitation signal having a wavelength from about 400 nm to about 490 nm to a retina of the eye;
- detecting, using one or more hyperspectral sensors, a first electromagnetic emissions spectrum from the retina in response to the first excitation signal;
- determining a first amount of drusen present in the retina by analyzing the first electromagnetic emissions spectrum to extract a first target emission spectrum from the first electromagnetic emissions spectrum separate from spectral characteristics of a retinal pigment epithelium (RPE) and a Bruch's membrane (BrM) of the patient's eye, wherein the first target emissions spectrum extends from a wavelength from about 450 nm to about 580 nm, and quantifying the first amount of drusen present in the retina based on the first target emissions spectrum;
- administering a second excitation signal having a wavelength from about 400 nm to about 490 nm to the retina subsequent to administration of the pharmaceutical treatment to the patient;
- detecting, using the one or more hyperspectral sensors, a second electromagnetic emissions spectrum from the retina in response to the second excitation signal;
- determining a second amount of drusen present in the retina by analyzing the second electromagnetic emissions spectrum to extract a second target emission spectrum from the second electromagnetic emissions spectrum separate from spectral characteristics of the RPE and the BrM of the patient's eye, wherein the second target emissions spectrum extends from a wavelength from about 450 nm to about 580 nm 180 nm to about 550 nm, and quantifying the second amount of drusen present in the retina based on the second target emissions spectrum; and
- determining the effectiveness of a pharmaceutical treatment for aged-related macular degeneration as a function of the first amount and the second amount of drusen detected.

* * * * *

UNITED STATES PATENT AND TRADEMARK OFFICE
CERTIFICATE OF CORRECTION

PATENT NO. : 10,314,473 B2  
APPLICATION NO. : 15/261102  
DATED : June 11, 2019  
INVENTOR(S) : Smith Page 1 of 1

It is certified that error appears in the above-identified patent and that said Letters Patent is hereby corrected as shown below:

In the Claims

Column 18, Line 14:
"wavelength from about 450 nm to about 580 inn; and" should read "wavelength from about 450 nm to about 580 nm; and".

Column 19, Line 28:
"patient's eve;" should read "patient's eye;".

Column 20, Lines 48 and 49:
"length from about 450 nm to about 580 nm 180 nm to about 550 nm, and quantifying the second amount of" should read "length from about 450 nm to about 580 nm, and quantifying the second amount of".

Signed and Sealed this  
Twenty-eighth Day of April, 2020

Andrei Iancu  
*Director of the United States Patent and Trademark Office*